United States Patent
Ulmann et al.

(10) Patent No.: US 12,234,237 B2
(45) Date of Patent: Feb. 25, 2025

(54) FOLATE SALTS

(71) Applicant: APROFOL AG, Appenzell Steinegg (CH)

(72) Inventors: Martin Ulmann, Dachsen (CH); Gerd Wiesler, Lohn (CH); Arthur Bodenmüller, Seltisberg (CH); Markus Müller

(73) Assignee: APROFOL AG (CH)

( * ) Notice: Subject to any disclaimer, the term of this patent is extended or adjusted under 35 U.S.C. 154(b) by 0 days.

(21) Appl. No.: 18/243,991

(22) Filed: Sep. 8, 2023

(65) Prior Publication Data

US 2023/0416253 A1 Dec. 28, 2023

Related U.S. Application Data

(63) Continuation of application No. 17/289,609, filed as application No. PCT/EP2019/079941 on Oct. 31, 2019, now Pat. No. 11,787,808.

(30) Foreign Application Priority Data

Oct. 31, 2018 (EP) ..................................... 18203849

(51) Int. Cl.
A61K 31/519 (2006.01)
A23L 33/10 (2016.01)
C07D 475/04 (2006.01)

(52) U.S. Cl.
CPC ............ *C07D 475/04* (2013.01); *A23L 33/10* (2016.08); *A61K 31/519* (2013.01); *C07B 2200/13* (2013.01)

(58) Field of Classification Search
CPC ..... C07D 475/04; A23L 33/10; A61K 31/519; C07B 2200/13; A61P 7/06; A61P 9/00; A61P 19/02; A61P 25/00

USPC ........................................................ 514/249
See application file for complete search history.

(56) References Cited

U.S. PATENT DOCUMENTS

| | | | |
|---|---|---|---|
| 5,382,581 A | 1/1995 | Marazza et al. |
| 5,710,271 A | 1/1998 | Felder et al. |
| 5,817,659 A | 10/1998 | Muller et al. |
| 6,441,168 B1 | 8/2002 | Muller et al. |
| 9,301,922 B1 | 4/2016 | Ulmann |
| 9,642,853 B2 | 5/2017 | Ulmann |

(Continued)

FOREIGN PATENT DOCUMENTS

| | | |
|---|---|---|
| CN | 1277197 A | 6/2004 |
| CN | 102775407 A | 8/2015 |

(Continued)

OTHER PUBLICATIONS

Gupta et al., "Salts of Therapeutic Agents: Chemical, Physicochemical, and Biological Considerations", Molecules, (Jul. 2018), vol. 23, No. 7, p. 1719, (15 pages).

(Continued)

*Primary Examiner* — Taylor V Oh
(74) *Attorney, Agent, or Firm* — NGUYEN TARBET IP LAW

(57) ABSTRACT

The invention relates to crystalline folate salts. The salt consists of a folate anion and an organic cation. The folate anion is 5-methyl-(6S)-tetrahydrofolic acid, and the cation is an organic compound which is an alkanolamine selected from the group consisting of choline, N-methylaminoethanol, 2-amino-2-methylpropanol and 2-dimethylaminoethanol.

11 Claims, 5 Drawing Sheets

(56) References Cited

U.S. PATENT DOCUMENTS

| | | |
|---|---|---|
| 10,370,350 B2 | 8/2019 | O'Neill et al. |
| 11,549,421 B2 | 1/2023 | Brück |
| 2011/0171134 A1 | 7/2011 | Iskandar et al. |
| 2016/0207925 A1 | 7/2016 | Fracchia |
| 2020/0030453 A1 | 1/2020 | Liu et al. |

FOREIGN PATENT DOCUMENTS

| | | |
|---|---|---|
| CN | 107304212 A | 10/2017 |
| CN | 111448196 A | 7/2020 |
| EP | 0626965 A1 | 12/1994 |
| EP | 3 461 826 A1 | 4/2019 |
| JP | H07-025876 A | 1/1995 |
| JP | 3162073 B2 | 4/2001 |
| JP | 2011-512366 A | 4/2011 |
| JP | 2016-532714 A | 10/2016 |
| JP | 2020-518655 A | 6/2020 |
| JP | 2021-510406 A | 4/2021 |
| WO | 9317022 A1 | 9/1993 |
| WO | 2009103333 A1 | 8/2009 |
| WO | 2009103334 A1 | 8/2009 |
| WO | 2018178142 A1 | 10/2018 |

OTHER PUBLICATIONS

Bastin et al., "Salt Selection and Optimization Procedures for Pharmaceutical New Chemical Entities". Organic Process Research & Development, (Jul. 19, 2000), vol. 4, No. 5, pp. 427-435.

Hirayama, "Crystallization Methods for Pharmaceuticals". Handbook for creation of crystals of organic compounds, (2008), pp. 17-23, 37-40, 45-51, 57-65.

Aldrich, Aldrich Catalogue, 1998-1999, pp. 89, 417 and 1082, 4 pages.

International Search Report and Written Opinion for International Application No. PCT/EP2019/079941, dated Mar. 18, 2020, 16 pages. 2021.

Entire patent prosecution history of U.S. Appl. No. 17/289,609, filed Apr. 28, 2021, entitled, "Folate Salts".

FOLATE SALTS

CROSS-REFERENCE TO RELATED APPLICATIONS

This is a continuation of U.S. application Ser. No. 17/289,609, filed Apr. 28, 2021, which is the U.S. National Phase application of PCT International Application No. PCT/EP2019/079941, filed Oct. 31, 2019, which claims the benefit of European Application No. 18203849.7, filed Oct. 31, 2018, the disclosures of each of which are incorporated by reference herein in their entireties for all purposes.

FIELD OF THE INVENTION

The invention relates to folate salts, their preparation and compositions comprising the same.

BACKGROUND OF THE INVENTION

Depression and other mental health disorders such as dementia, autism, ADHD and Alzheimer, as well as chronic non-communicable diseases (NCDs) such as diabetes type 1 and 2, vascular diseases, and cancer are a growing burden for patients and the health care systems, especially in view of the aging population. There are various reasons for these different diseases; however, as a common risk factor a suboptimal folate-status has been found, in the whole body or in specific tissues.

It is well known that vitamins of the B-complex group are involved in numerous metabolic processes of the body, e.g. in the conversion of carbohydrates into glucose, which is metabolized to produce energy. These vitamins are further essential in the breakdown of fats and proteins and play an important role in maintaining muscle tone along the lining of the digestive tract and promoting health of the nervous system, and e.g. eyes, skin, hair, liver and kidney.

In addition, it is known that folate is compulsory in the production and maintenance of new cells. Especially important in times of rapid cell division and growth such as infancy and pregnancy. Folate is needed to replicate DNA. Thus, folate deficiency hinders DNA synthesis and cell division, affecting most clinically the bone marrow, a site of rapid cell turnover. Because RNA and protein synthesis is not hindered, large red blood cells, i.e. megaloblasts, are produced, resulting in macrocytic anemia, such as megaloblastic anemia, as may be seen in celiac disease, and in anemias of nutritional origin, or in pregnancy, infancy, or childhood. Accordingly, both adults, especially elderly, and children need folate to make normal red blood cells and prevent anemia. Folate also helps prevent changes to DNA that may lead to cancer.

Folate derivatives such as diverse tetrahydrofolic acid derivatives may also be used as drug or as basic substance for the preparation of other derivatives. Yet, also tetrahydrofolic acid and the derivatives thereof are known to possess an extreme instability, particularly due to their susceptibility to oxidation. In particular, 5-formyltetrahydrofolic acid (Folinic acid, Leucovorin) and its biologically active 5-formyl-(6S) form has importance as a drug ingredient mainly in oncology, as concomitant therapy with methotrexate and 5-fluorouracil treatment, and in the treatment of folate deficiency anemia associated with pregnancy, antibiotic therapy etc. Among folates and reduced folates, the calcium salts can be mentioned as the most relatively stable derivatives: U.S. Pat. Nos. 5,817,659 and 6,441,168 disclose crystalline salts, preferably calcium salts, of 5-methyl-(6R, S)-, (6S)- or (6R)-tetrahydrofolic acid having a water of crystallization of at least one equivalent per equivalent of said acid. 5-methyltetrahydrofolate is the only folic acid derivative on the market which can directly penetrate the blood/brain barrier without further metabolism. Naturally occurring 5-methyltetrahydrofolic acid is solely in the 6S form; the 6R form is considered biochemically inactive and is excreted through the kidney. Besides, several compositions for human and animal consumption, comprising either folates and/or reduced folates, have been reported, in various forms and together with vitamins, arginine, lysine, thiamine and/or other active ingredients, either as a nutritional supplement or for the treatment and prevention of various diseases such as, for instance, neurological, pathophysiological, cardiovascular diseases, arthritic and inflammation conditions.

Various folate salts are known. In general, these salts comprise a folate and an inorganic cation such as calcium and magnesium. These alkaline earth metal cations are inert insofar that they themselves do not show any pharmacological effect in humans. The scarce solubility in aqueous solutions of such salts has been widely reported. Aqueous compositions with improved solubility and stability of folates have been disclosed, e.g. in U.S. Pat. Nos. 9,301,922 and 9,642,853.

U.S. Pat. No. 5,382,581 discloses diastereomer separation of 5-methyl-tetrahydrofolic acid using ammonium salts. WO 2018/178142 describes binary salts of 5-methyl-tetrahydrofolic acid comprising sodium and an organic base. US 2016/0207925 discloses salts of L-methyl-folate comprising amino acids such as L-arginine and L-asparagine. The salts are lyophilized and appear to be amorphous. U.S. Pat. No. 5,710,271 describes a process for the preparation, separation and purification of (6S) and (6R) diastereomers of folinic acid. Further, WO 2009/103334 discloses freeze or spray dried glucosamine and galactosamine salts of L-methyltetrahydrofolate. WO 2009/103333 describes a process for the separation of (6R) and (6S) diastereomers of 5-methyltetrahydrofolic acid using an organic base in the form of a phenylethyl-amine or a naphthylethyl-amine compound to obtain pure and stable diastereomers. CN 107304212 discloses a process for the preparation of amorphous L-methyltetrahydrofolate amino acid salts. WO 93/17022 describes a process for the separation of stereoisomers of folinic acid. The separation is achieved by salification of (R/S) folinic acid with a di- or polyamines and subsequent selective crystallization of the (6S) diastereomer of folinic acid.

In addition, numerous compositions of folates comprising folates and further compounds such as vitamins, lysine, thiamin and other active ingredients have been described. However, stable salts of folates with a good solubility in water and also in organic solvents would allow more versatile pharmaceutical compositions.

SUMMARY

The object of the present invention is to provide folate salts combining a further active compound and showing a good stability and a good solubility in water and also in apolar solvents.

The object is achieved by a crystalline folate salt comprising, consisting of or consisting essentially of a tetrahydrofolic acid anion and an organic cation wherein the anion is 5-methyl-(6S)-tetrahydrofolic acid, and the cation is an organic compound wherein the organic compound is an alkanolamine selected from the group consisting of choline, 2-dimethylaminoethanol, N-methylaminoethanol, and 2-amino-2-methylpropanol. Further preferred embodiments are disclosed in the detailed description that follows.

DETAILED DESCRIPTION

As a high solubility in an apolar solvent is considered a solubility of higher than 2 weight-% (w/w) of a particular folate salt in a particular organic or apolar solvent based on the total weight of the solution. Solubility has been determined at 20° C. Apolar solvents or mixtures thereof are for instance glycerol, methanol, ethanol, 1-propanol, 2-propanol and dimethylsulfoxid (DMSO). Apolar solvents are understood as dry solvents, that is without any water content. Apolar solvents may be pure solvents, comprising only one type of apolar solvent or it may be a mixture of at least two of the aforementioned apolar solvents. Polarity is in comparison to the polarity of water.

A high degree of crystallinity means that the crystalline content of the folate salt is higher than 40% based on the total amount of the folate salt. Thus, a crystalline folate salt is understood as a folate salt having crystalline content of more than 40%. The degree of crystallinity is determined by X-ray diffraction (XRD) analysis.

A folate salt according to the present invention consists of a tetrahydrofolic acid anion and an organic cation. The anion is a folate, preferably 5-methyl-(6S)-tetrahydrofolic acid. Further, the cation is an organic compound wherein the organic compound is an alkanolamine which is selected from the group consisting of choline, N-methylaminoethanol, 2-amino-2-methylpropanol or 2-dimethyl-aminoethanol.

A crystalline folate salt according to claim 1, wherein the folate salts have a high solubility in organic solvents. A high solubility in organic solvents is understood as a solubility of more than 2 weight-% based on the total weight of the solution.

In a further embodiment the anion of the folate salt may also be 5-formyl-(6S)-tetrahydrofolic acid. Possible organic cations are selected from the same group, i.e. from the group consisting of choline, N-methyl-aminoethanol, 2-dimethyl-aminoethanol, and 2-amino-2-methyl-propanol.

Crystalline folate salts according to the present invention show a high stability and also a high solubility in water and apolar solvents.

An additional counter-ion for the anions of the folate salt, 5-formyl-(6S)-tetrahydrofolic acid or 5-methyl-(6S)-tetrahydrofolic acid, may be the organic cation arginine.

In a preferred embodiment, the crystalline folate salt consists of tetrahydrofolic acid anion and an organic cation. The anion is 5-methyl-(6S)-tetrahydrofolic acid. The cation is di-choline.

In another embodiment, the crystalline folate salt consists of tetrahydrofolic acid anion and an organic cation, wherein the anion is 5-methyl-(6S)-tetrahydrofolic acid, and wherein the cation is mono-2-dimethylaminoethanol.

In another embodiment, the crystalline folate salt consists of tetrahydrofolic acid anion and an organic cation, wherein the anion is 5-methyl-(6S)-tetrahydrofolic acid, and wherein the cation is N-methyl aminoethanol.

In further embodiment, the crystalline folate salt consists of tetrahydrofolic acid anion and an organic cation, wherein the anion is 5-methyl-(6S)-tetrahydrofolic acid, and wherein the cation is 2-amino-2-methylpropanol.

In a further embodiment, the crystalline folate salt consists of the tetrahydrofolic acid anion is 5-methyl-(6S)-tetrahydrofolic acid and the organic cation is di-choline, wherein the $^1$H-NMR shifts in D$_2$O are

| δ (1H) in ppm | Multiplicity | Intensity |
|---|---|---|
| 7.60 | d | 2H |
| 6.68 | d | 2H |
| 4.24 | m | 1H |
| 3.98 | m | 4H |
| 3.44 | m | 1H |
| 3.43 | m | 4H |
| 3.25 | m | 1H |
| 3.11 | s | 18H |
| 3.10 | m | 1H |
| 3.01 | m | 1H |
| 2.91 | m | 1H |
| 2.47 | s | 3H |
| 2.24 | m | 2H |
| 2.09 | m | 1H |
| 1.96 | m | 1H |

In a further embodiment, the crystalline tetrahydrofolic acid salt consists of the tetrahydrofolic acid anion is 5-methyl-(6S)-tetrahydrofolic acid and the organic cation is di-2-dimethylaminoethanol wherein the $^1$H-NMR shifts in D$_2$O are

| δ (1H) in ppm | Multiplicity | Intensity |
|---|---|---|
| 7.56 | d | 2H |
| 6.65 | d | 2H |
| 4.19 | m | 1H |
| 3.77 | t | 4H |
| 3.40 | dd | 1H |
| 3.20 | d | 1H |
| 3.14 | t | 4H |
| 3.03 | m | 1H |
| 2.98 | m | 1H |
| 2.88 | m | 1H |
| 2.78 | s | 12H |
| 2.42 | s | 3H |
| 2.19 | m | 2H |
| 2.04 | m | 1H |
| 1.90 | m | 1H |

In a further embodiment, the crystalline tetrahydrofolic acid salt consists of the tetrahydrofolic acid anion is 5-methyl-(6S)-tetrahydrofolic acid and the organic cation is mono-2-dimethylaminoethanol wherein the $^1$H-NMR shifts in D$_2$O are

| δ (1H) in ppm | Multiplicity | Intensity |
|---|---|---|
| 7.52 | d | 2H |
| 6.67 | d | 2H |
| 4.22 | m | 1H |
| 3.77 | t | 2H |
| 3.54 | d | 1H |
| 3.44 | m | 1H |
| 3.36 | d | 1H |
| 3.16 | t | 2H |
| 3.13 | m | 2H |
| 2.80 | s | 6H |
| 2.72 | s | 3H |
| 2.25 | m | 2H |
| 2.08 | m | 1H |
| 1.93 | m | 1H |

In a further embodiment, the crystalline tetrahydrofolic acid salt consists of the tetrahydrofolic acid anion is 5-methyl-(6S)-tetrahydrofolic acid and the organic cation is di N-methylaminoethanol wherein the $^1$H-NMR shifts in D$_2$O are

| δ (1H) in ppm | Multiplicity | Intensity |
| --- | --- | --- |
| 7.55 | d | 2H |
| 6.64 | d | 2H |
| 4.19 | m | 1H |
| 3.73 | t | 4H |
| 3.39 | dd | 1H |
| 3.19 | d | 1H |
| 3.06 | t | 4H |
| 3.01 | m | 1H |
| 2.96 | m | 1H |
| 2.86 | m | 1H |
| 2.63 | s | 6H |
| 2.41 | s | 3H |
| 2.20 | m | 2H |
| 2.04 | m | 1H |
| 1.92 | m | 1H |

In a further embodiment, the crystalline tetrahydrofolic acid salt consists of the tetrahydrofolic acid anion is 5-methyl-(6S)-tetrahydrofolic acid and the organic cation is di 2-amino-2-methyl propanol wherein the $^1$H-NMR shifts in $D_2O$ are

| δ (1H) in ppm | Multiplicity | Intensity |
| --- | --- | --- |
| 7.61 | d | 2H |
| 6.70 | d | 2H |
| 4.25 | m | 1H |
| 3.49 | s | 4H |
| 3.45 | dd | 1H |
| 3.25 | d | 1H |
| 3.08 | m | 1H |
| 2.93 | m | 1H |
| 2.48 | s | 3H |
| 2.24 | m | 2H |
| 2.09 | m | 1H |
| 1.96 | m | 1H |
| 1.25 | s | 1H |

In a further preferred embodiment, a pharmaceutical composition comprises at least one folate salt according to the present invention as the main active compound. The composition further comprises at least a pharmaceutically acceptable excipient. The composition may for instance comprise a buffer compound. Suitable and preferred buffer compounds are trometamol and HEPES. Further, an antioxidant compound may be present in the composition. Preferred antioxidant compounds are thioglycerol, dithiothreitol (DTT) and cysteine.

Further, the at least one folate salt according to the present invention is used for the preparation of a medicament, a food additive or a nutritional supplement, for the prevention and/or treatment of either deficiencies or disorders that are positively affected by the administration of a folate salt. There are a number of disease conditions which are positively influenced by compositions comprising folate salts. Such diseases are for instance pathophysiological, neurological and inflammatory diseases.

In addition, a method for preparing the crystalline folate salt according to the present invention, said tetrahydrofolic acid salt consisting of a folate acid anion and an organic cation, comprises the step of adding oxalic acid, alternatively a fluoride salt or directly from the free compounds to an aqueous composition of folate earth alkaline metal salts or free folate acid.

Surprisingly, crystallization was achieved from organic solvents, such as 1-propanol, comprising a limited amount of water, for instance less than 12 weight-% of water, preferably less than 10 weight-% of water. The weight-% of water are based on the total weight of the organic solvent and water. The minimal amount of water is a quantity corresponding to 0.2 weight-% of water in organic solvent. This corresponds to 1 to 170 crystal water equivalents based on the molar quantity of folate. In the isolated folate salts 1.5 to 2 water of crystallization are detected. The organic or apolar solvents are understood to be dry, i.e. comprising no water. Without the water added to the organic solvents in the afore-mentioned quantities, all folate salts precipitate in amorphous form.

BRIEF DESCRIPTION OF THE DRAWINGS

The crystalline folate salts according to the present invention are further described in the figures, in which.

EXAMPLES

Example 1

Figure 1:
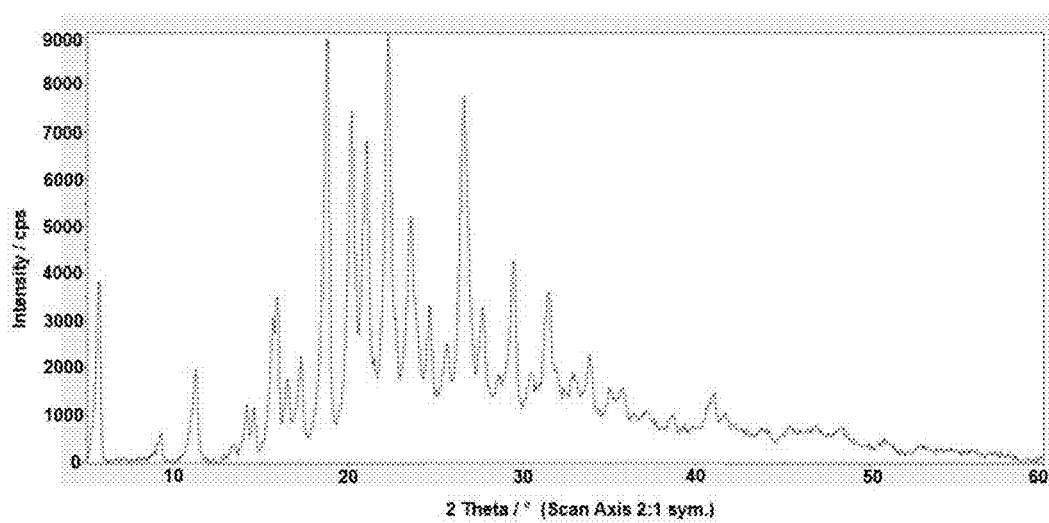
FIG. 1 shows the X-ray diffractogram of 5-Methyl-(6S)-tetrahydrofolic acid di Choline salt of example 1.
Figure 2:
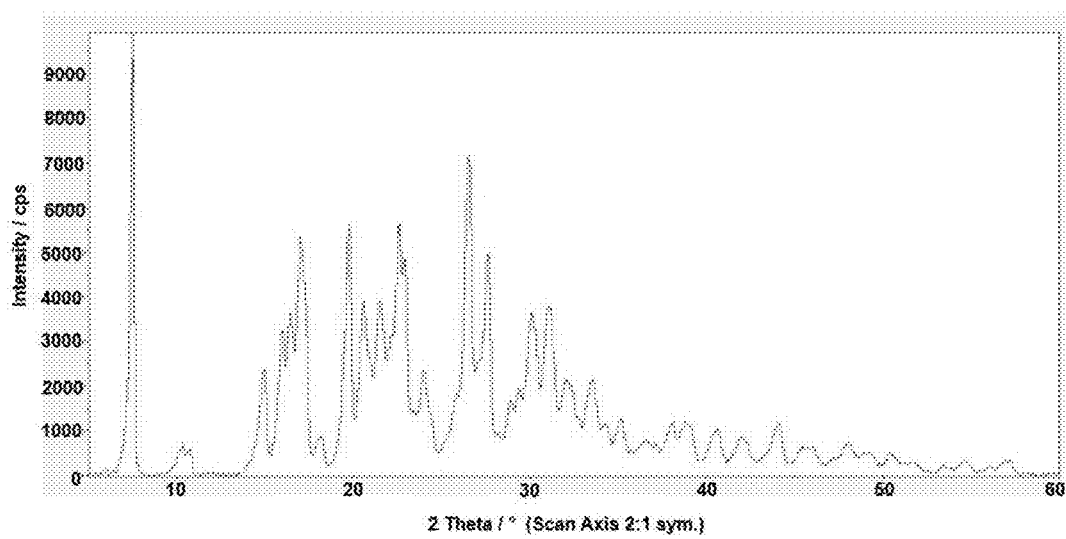
FIG. 2 shows the X-ray diffractogram of 5-Methyl-(6S)-tetrahydrofolic acid mono 2-Dimethylaminoethanol salt of example 3.
Figure 3:
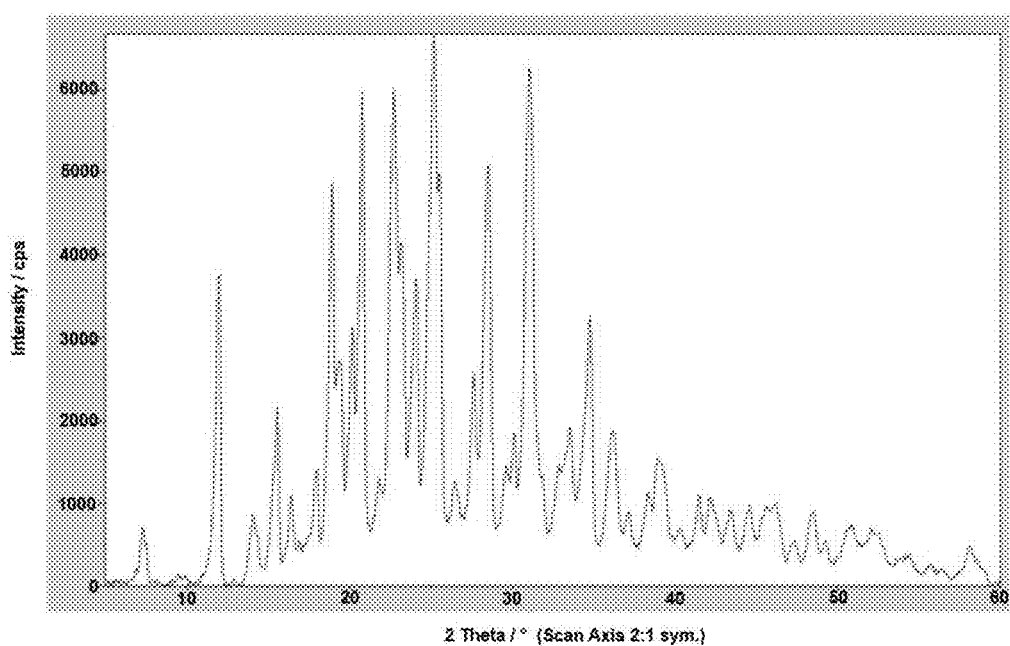
FIG. 3 shows the X-ray diffractogram of 5-Methyl-(6S)-tetrahydrofolic acid di-2-dimethylaminoethanol salt of example 4.
Figure 4:
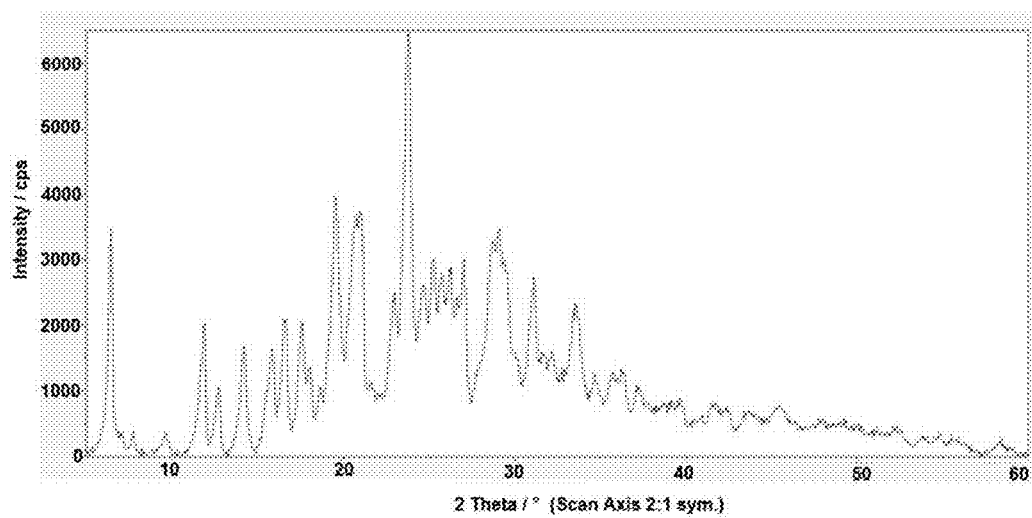
FIG. 4 shows the X-ray diffractogram of 5-Methyl-(6S)-tetrahydrofolic acid di N-methylaminoethanol salt of example 5.
Figure 5:
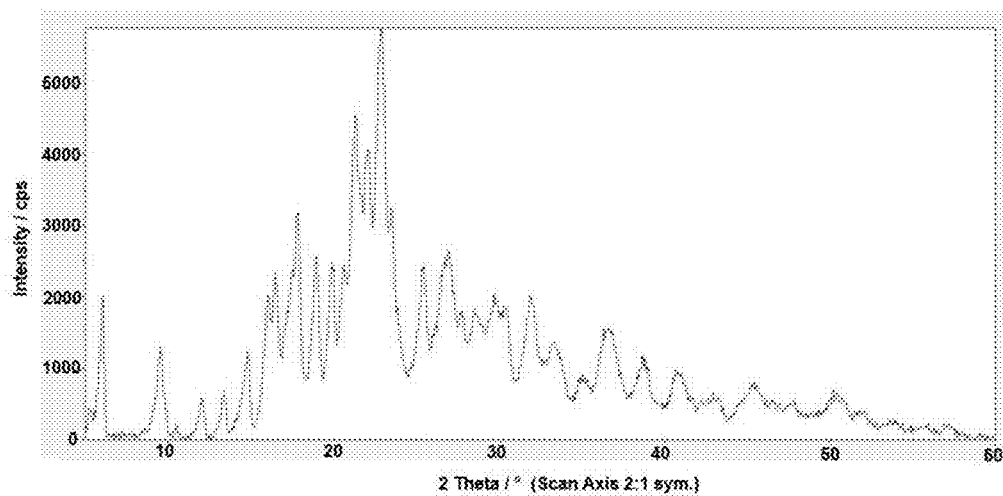
FIG. 5 shows the X-ray diffractogram of 5-Methyl-(6S)-tetrahydrofolic acid di 2-Amino-2-methyl propanol salt of example 6.

Preparation of 5-Methyl-(6S)-tetrahydrofolic acid di Choline salt 7.00 g (15.23 mmol) of Levomefolic acid was suspended under argon in 70 ml 1-propanol and brought to reflux. Then 7.71 ml (31.99 mmol) of a 47% aqueous solution of cholinhydroxide was added and the mixture stirred under reflux until a clear solution is formed. Then an additional 80 ml 1-propanol was added resulting in a Water concentration in 1-propanol of 3.2% w/w and the solution seeded with a crystalline sample of product. After crystallization sets in at 65° C., the suspension was slowly cooled down from 65° C. to 2-8° C. The suspension was stirred slowly at 2-8° C. for additional 2 h. The grainy crystals were sucked off, washed with cooled 1-propanol and dried to give 7.29 g of the white crystalline crude title compound. Recrystallization under Argon of 7.29 g crude title compound by dissolving in ca 130 ml methanol at 60° C. and evaporated at 60° C. vacuum. The remainder was taken-up in ca 60 ml of 1-propanol and dissolved at 60° C. followed by concentration to final mass of 40 g solution. At 70° C. temperature of the oil bath, the solution was diluted under argon with 22 ml of a mixture of 1-propanol and water (20:2% v/v) at 70° C. (ca 4.0% water in 1-propanol) while from the pale-yellow solution after seeding crystallization started. The temperature of the suspension was stepwise lowered to 20° C. and the crystallization completed by slowly stirring at 2-8° C. The isolated crystals were dried at 60° C./<1 mbar and yielded 5.76 g MTHF di-choline. Analytical data:

| δ (1H) in ppm | Multiplicity | Intensity |
|---|---|---|
| 7.60 | d | 2H |
| 6.68 | d | 2H |
| 4.24 | m | 1H |
| 3.98 | m | 4H |
| 3.44 | m | 1H |
| 3.43 | m | 4H |
| 3.25 | m | 1H |
| 3.11 | s | 18H |
| 3.10 | m | 1H |
| 3.01 | m | 1H |
| 2.91 | m | 1H |
| 2.47 | s | 3H |
| 2.24 | m | 2H |
| 2.09 | m | 1H |
| 1.96 | m | 1H |

Optical rotation: $\alpha^{20D}$ +33.6° (c=1 $H_2O$)
Crystal water in MTHF di choline: 1.6 calculated (water analysis by Karl Fischer (KF) & microanalysis)
Melting point: 232-233° C. (Differential Scanning Calorimetry (DSC))
X-Ray Diffraction Analysis:
Peaklist of the Diffractogram

| No | d | Ang-COG | I-net | FWHM | I-rel | J-Net | 2-Theta |
|---|---|---|---|---|---|---|---|
| 1 | 17.6149 | 5.8155 | 5088.65 | 0.2764 | 90 | 1878.05 | 5.8216 |
| 2 | 11.0451 | 9.2958 | 320.35 | 0.3760 | 6 | 131.19 | 9.2905 |
| 3 | 8.9627 | 11.4563 | 2097.97 | 0.3840 | 37 | 936.77 | 11.4556 |
| 4 | 7.5765 | 13.5529 | 202.00 | 18.7226 | 4 | 99.96 | 13.5607 |
| 5 | 7.2373 | 14.1992 | 460.41 | 0.8508 | 8 | 210.93 | 14.1994 |
| 6 | 7.0149 | 14.6342 | 431.98 | 0.2524 | 8 | 158.36 | 14.6520 |
| 7 | 6.5167 | 15.8216 | 1653.76 | 0.6104 | 29 | 1058.96 | 15.7790 |
| 8 | 6.2150 | 16.5491 | 642.99 | 0.4488 | 11 | 283.29 | 16.5503 |
| 9 | 5.9229 | 17.3469 | 1017.17 | 0.5232 | 18 | 528.76 | 17.3726 |
| 10 | 5.4527 | 18.8774 | 4992.44 | 0.4222 | 89 | 2396.55 | 18.8837 |
| 11 | 5.0753 | 20.3057 | 4352.89 | 0.4341 | 77 | 2195.14 | 20.3023 |
| 12 | 4.8661 | 21.1764 | 3407.01 | 0.5204 | 60 | 1822.80 | 21.1853 |
| 13 | 4.5973 | 22.4387 | 5633.15 | 0.4240 | 100 | 2708.02 | 22.4395 |
| 14 | 4.3384 | 23.7939 | 3535.90 | 0.4618 | 63 | 1925.41 | 23.7973 |
| 15 | 4.1694 | 24.7637 | 1239.98 | 0.4101 | 22 | 541.98 | 24.7769 |
| 16 | 4.0087 | 25.7760 | 831.56 | 0.4382 | 15 | 402.18 | 25.7869 |
| 17 | 3.8590 | 26.8120 | 4491.21 | 0.6178 | 80 | 2982.56 | 26.8056 |
| 18 | 3.7175 | 27.8443 | 1414.54 | 0.4184 | 25 | 694.71 | 27.8460 |
| 19 | 3.5012 | 29.6028 | 1823.55 | 0.5013 | 32 | 1058.01 | 29.6045 |
| 20 | 3.3931 | 30.6227 | 412.39 | 0.4148 | 7 | 168.97 | 30.5706 |
| 21 | 3.2818 | 31.6322 | 1712.11 | 0.4989 | 30 | 981.56 | 31.6337 |
| 22 | 3.1495 | 32.9955 | 320.51 | 0.5653 | 6 | 172.45 | 33.0000 |
| 23 | 3.0569 | 34.0194 | 898.90 | 0.4588 | 16 | 452.57 | 34.0292 |
| 24 | 2.9605 | 35.1572 | 336.68 | 8.2202 | 6 | 108.43 | 35.1733 |
| 25 | 2.9049 | 35.8675 | 545.60 | 1.0527 | 10 | 461.69 | 35.8695 |
| 26 | 2.8069 | 37.2239 | 258.37 | 0.6132 | 5 | 138.86 | 37.1657 |
| 27 | 2.6910 | 38.8121 | 270.28 | 0.4102 | 5 | 111.54 | 38.8293 |
| 28 | 2.5469 | 41.0925 | 600.58 | 0.8281 | 11 | 485.46 | 41.1230 |
| 29 | 2.5010 | 41.8533 | 371.98 | 0.4503 | 7 | 268.17 | 41.9128 |
| 30 | 2.3851 | 43.9497 | 172.63 | 0.5625 | 3 | 88.56 | 44.0533 |
| 31 | 2.2799 | 46.1501 | 262.73 | 1.2852 | 5 | 291.03 | 46.2000 |
| 32 | 2.2304 | 47.2739 | 338.31 | 0.9782 | 6 | 625.42 | 47.2871 |
| 33 | 2.0761 | 50.9480 | 174.51 | 0.6686 | 3 | 106.27 | 51.0446 |

Solubilities:

| L-MTHF di Choline | Methanol | Ethanol | 1-Propanol | DMSO | Glycerol |
|---|---|---|---|---|---|
| as % w/w | 38.7% | 0.3% | 0.2% | 31.3% | 24.1% |

The solubility of crystalline di choline in organic solvents shows a very differentiated picture and seems to be dependent on the degree of crystallinity. If the di choline folate salt is highly crystalline or in other words has a high crystalline content the solubility of the di choline folate salt in ethanol is low, 0.3 weight-% based on the total weight of the solution. At a high amorphous content, the solubility of the di choline folate salt in ethanol is very high (38.8 weight-%). Further, in mixtures of organic solvents, e.g. ethanol with 5 weight-% methanol or glycerol based on the total weight of the solution, the solubility of the highly crystalline di choline folate salt is enhanced, and rises up to 25 weight-% (based on the total weight of the solution). A high degree of crystallinity means that the crystalline content of the folate salt is higher than 40% based on the total amount of the folate salt. A high solubility in a solvent means that the folate salt is soluble in an amount of more than 2 weight-% based on the total weight of the solution.

Example 2

Preparation of 5-Methyl-(6S)-tetrahydrofolic acid di Choline salt 13.72 g (28.9 mmol) of Levomefolic acid was suspended under argon in 70 ml methanol at 20-22° C. Then 160 ml (57.6 mmol, 0.360 mol/l in 1-propanol) of choline hydroxide solution was added at 20-22° C. during ca 3 mins, rinsed with 4 ml 1-propanol and the mixture stirred at 20-22° C. until a clear solution is formed. Then an additional 13.5 ml 1-propanol was added and the reaction mixture evaporated at 50° C./50 mbar followed by co-evaporation twice with 11 ml 1-propanol resulting in 43.6 g remainder. The remainder was diluted with 140 ml 1-propanol under argon and heated to 65° C. external temperature. Addition of seed crystals and 5.25 ml water was added slowly at 65° C. till turbidity lasts (ca 3.7% w/w water) while crystallization starts. The mixture was stirred, and the temperature reduced over 20 mins to 50° C., then was left cooling to 30° C. and the formed thick suspension stirred for 70 mins at 2-8° C. The crystals were isolated, washed with 4 ml of a mixture of 1-propanol/water 31:1 (v/v) and 24 ml 1-propanol and dried at 45-60° C./50-5 mbar yielding in 16.1 g L-MTHF di-choline. Analytical data:

| δ (1H) in ppm | Multiplicity | Intensity |
|---|---|---|
| 7.60 | d | 2H |
| 6.68 | d | 2H |
| 4.24 | m | 1H |
| 3.98 | m | 4H |
| 3.44 | m | 1H |
| 3.43 | m | 4H |
| 3.25 | m | 1H |
| 3.11 | s | 18H |
| 3.10 | m | 1H |
| 3.01 | m | 1H |
| 2.91 | m | 1H |
| 2.47 | s | 3H |
| 2.24 | m | 2H |
| 2.09 | m | 1H |
| 1.96 | m | 1H |

Crystal water in L-MTHF di choline: 2.0 calculated (KF & microanalysis)
Melting point: 232-233° C. (DSC)

Example 3

Preparation of 5-Methyl-(6S)-tetrahydrofolic Acid Mono 2-Dimethylaminoethanol Salt 2.00 g (4.353 mmol) of Levomefolic acid was placed under argon in 20 ml water, with a small amount of cysteine and heated to 70° C. This suspension was then treated with 876 μl (8.706 mmol, 2 equivalents) of 2-dimethylaminoethanol and stirred at 70° C. until a clear solution is formed. Isopropanol is then added gradually, at 70° C. for a total of 150 ml. When turbidity is reached, further 70 ml 2-propanol was added, and the mixture was treated with seeding crystals to initiate crystallization ca. 60° C. (ca 10.4% water in 2-propanol). The mixture was then slowly and gradually cooled down from 60° C. to 2-8° C. The crystals were sucked off, washed with cooled 2-propanol and dried under vacuum at 50° C. to give 1.96 g of the title compound as white crystals. Analytical data:

| δ (1H) in ppm | Multiplicity | Intensity |
|---|---|---|
| 7.52 | d | 2H |
| 6.57 | d | 2H |
| 4.22 | m | 1H |
| 3.77 | t | 2H |
| 3.54 | d | 1H |
| 3.44 | m | 1H |
| 3.36 | d | 1H |
| 3.16 | t | 2H |
| 3.13 | m | 2H |
| 2.80 | s | 6H |
| 2.72 | s | 3H |
| 2.25 | m | 2H |
| 2.08 | m | 1H |
| 1.93 | m | 1H |

Optical rotation: $\alpha^{20D}$ +11.0° (c=1 $H_2O$)
Crystal water in L-MTHF mono dimethylaminoethanol (L-MTHF mono deanol): 1.5 (Thermogravimetry (TG)), KF and microanalysis)
Melting point: 194° C. (DSC)
X-Ray Diffraction Analysis:
Peaklist of the Diffractogram

| No | d | Ang-COG | I-net | FWHM | I-rel | J-Net | 2-Theta |
|---|---|---|---|---|---|---|---|
| 1 | 13.6684 | 7.5233 | 9470.26 | 0.2310 | 100 | 2894.68 | 7.5046 |
| 2 | 9.9307 | 10.3232 | 710.95 | 0.9077 | 8 | 391.22 | 10.3357 |
| 3 | 9.5756 | 10.6907 | 607.82 | 0.3028 | 6 | 223.97 | 10.7202 |
| 4 | 6.8805 | 14.9391 | 2380.98 | 0.4596 | 25 | 1418.01 | 14.9399 |
| 5 | 8.4302 | 15.9944 | 3163.04 | 1.4612 | 33 | 1670.87 | 15.9927 |
| 6 | 6.2593 | 16.4307 | 3578.72 | 1.1601 | 38 | 1774.58 | 16.4324 |
| 7 | 6.0417 | 17.0682 | 5216.61 | 0.7659 | 55 | 3394.07 | 17.0285 |
| 8 | 5.6543 | 18.1396 | 688.23 | 0.5915 | 7 | 386.13 | 18.2046 |
| 9 | 5.2111 | 19.7680 | 5319.67 | 0.4234 | 56 | 2626.57 | 19.7678 |
| 10 | 5.0039 | 20.5988 | 3591.46 | 0.9940 | 38 | 2020.87 | 20.5952 |
| 11 | 4.7911 | 21.5345 | 3548.03 | 2.5379 | 37 | 2461.35 | 21.5206 |
| 12 | 4.5649 | 22.6170 | 5248.67 | 0.9850 | 55 | 3189.16 | 22.6006 |
| 13 | 4.5039 | 22.8777 | 4508.99 | 0.3774 | 48 | 1819.76 | 22.9112 |
| 14 | 4.2998 | 24.0040 | 1881.06 | 0.7021 | 20 | 1387.73 | 24.0146 |
| 15 | 3.8953 | 26.5510 | 6463.28 | 0.4562 | 68 | 3957.98 | 26.5512 |
| 16 | 3.7459 | 27.6194 | 4178.32 | 0.4823 | 44 | 2546.21 | 27.6310 |
| 17 | 3.5812 | 28.9363 | 828.80 | 0.5346 | 9 | 337.51 | 28.9290 |
| 18 | 3.5247 | 29.4240 | 1073.85 | 1.0007 | 11 | 464.63 | 29.4025 |
| 19 | 3.4418 | 30.1524 | 2737.43 | 0.7015 | 29 | 1965.10 | 30.1279 |
| 20 | 3.3365 | 31.1067 | 2846.76 | 0.6751 | 30 | 1995.56 | 31.1023 |
| 21 | 3.2373 | 32.1615 | 1268.85 | 0.8297 | 13 | 1096.14 | 32.0799 |
| 22 | 3.0986 | 33.5359 | 1322.74 | 0.6567 | 14 | 887.70 | 33.5578 |
| 23 | 3.0374 | 34.2707 | 429.00 | 0.4830 | 5 | 206.19 | 34.2546 |
| 24 | 2.9597 | 35.1596 | 638.14 | 0.4725 | 7 | 307.71 | 35.1834 |
| 25 | 2.8488 | 36.5824 | 366.65 | 0.7608 | 4 | 242.21 | 36.5996 |
| 26 | 2.8112 | 37.1123 | 320.16 | 7.7613 | 3 | 147.22 | 37.1069 |
| 27 | 2.7396 | 38.0825 | 844.44 | 0.8266 | 9 | 555.29 | 38.1133 |
| 28 | 2.6887 | 38.8946 | 861.16 | 0.8635 | 9 | 742.31 | 38.8641 |
| 29 | 2.5774 | 40.5869 | 709.00 | 0.6395 | 7 | 470.99 | 40.6144 |
| 30 | 2.4903 | 42.0647 | 537.66 | 0.7464 | 6 | 413.92 | 42.1022 |
| 31 | 2.3835 | 44.0766 | 910.34 | 0.6219 | 10 | 622.66 | 44.0852 |
| 32 | 2.2878 | 45.8070 | 416.47 | 1.0787 | 4 | 430.76 | 46.0321 |
| 33 | 2.1983 | 48.0532 | 495.68 | 0.7232 | 5 | 503.50 | 48.0218 |
| 34 | 2.1442 | 49.1828 | 301.25 | 0.4741 | 3 | 266.76 | 49.3120 |
| 35 | 2.0995 | 50.4760 | 322.22 | 0.5887 | 3 | 205.42 | 50.4360 |
| 36 | 1.9899 | 53.4212 | 165.35 | 0.5816 | 2 | 83.60 | 53.4250 |
| 37 | 1.9451 | 54.7129 | 268.96 | 0.7281 | 3 | 192.90 | 54.7570 |
| 38 | 1.9033 | 56.0921 | 150.49 | 1.1681 | 2 | 106.89 | 56.0650 |
| 39 | 1.8676 | 57.1017 | 325.25 | 0.9212 | 3 | 353.38 | 57.2340 |

Solubilities:

| L-MTHF mono deanol | Methanol | Ethanol | 1-Propanol | DMSO | Glycerol |
|---|---|---|---|---|---|
| as % w/w | 2.5 | 0.2 | 0.2 | 24.8 | 10.0 |

Example 4

Preparation of 5-Methyl-(6S)-tetrahydrofolic acid di 2-Dimethylaminoethanol salt 2.00 g (4.353 mmol) of Levomefolic acid was placed under argon in 20 ml 1-propanol and heated to reflux while added 800 μl water. This suspension was then treated with 876 μl (8.706 mmol, 2 equivalents) of 2-dimethylaminoethanol, diluted with 3.2 ml Water and stirred at 100° C. until a clear solution is formed. 1-propanol (7 ml) is then added and the solvent evaporated at 40° C. in vacuum. The remainder (3.68 g) is dissolved in 30 ml 2-propanol/10 ml water and concentration by distilling off solvent at 40° C. in vacuum until crystallization starts. The crystals are ultrasonicated in 1-propanol for 5 mins at 20-25° C., suction filtered, washed 3× with 1-propanol and dried at 60° C./<1 mbar to give 2.34 g of the title compound as white crystals. Analytical data:

| δ (1H) in ppm | Multiplicity | Intensity |
|---|---|---|
| 7.56 | d | 2H |
| 6.65 | d | 2H |
| 4.19 | m | 1H |
| 3.77 | t | 4H |
| 3.40 | dd | 1H |
| 3.20 | d | 1H |
| 3.14 | t | 4H |
| 3.03 | m | 1H |
| 2.98 | m | 1H |
| 2.88 | m | 1H |
| 2.78 | s | 12H |
| 2.42 | s | 3H |
| 2.19 | m | 2H |
| 2.04 | m | 1H |
| 1.90 | m | 1H |

Optical rotation: $\alpha^{20D}$ +31.6° (c=1 $H_2O$)
Melting point: 157° C. (DSC)
X-Ray Diffraction Analysis:
Peaklist of the Diffractogram

| No | d | Ang-COG | I-net | FWHM | I-rel | J-Net | 2-Theta |
|---|---|---|---|---|---|---|---|
| 1 | 14.0264 | 7.3221 | 684.16 | 0.4542 | 12 | 350.96 | 7.3128 |
| 2 | 10.7387 | 9.5124 | 147.39 | 0.3087 | 3 | 99.32 | 9.5562 |
| 3 | 8.5793 | 11.9659 | 3827.45 | 0.3113 | 65 | 1509.53 | 11.9695 |

-continued

| No | d | Ang-COG | I-net | FWHM | I-rel | J-Net | 2-Theta |
|---|---|---|---|---|---|---|---|
| 4 | 7.3055 | 14.0683 | 783.85 | 0.5613 | 13 | 422.23 | 14.0662 |
| 5 | 6.6092 | 15.5602 | 1894.13 | 0.4137 | 32 | 806.64 | 15.5568 |
| 6 | 6.2563 | 16.4475 | 758.74 | 0.2929 | 13 | 252.74 | 16.4401 |
| 7 | 5.7290 | 17.9585 | 914.79 | 0.2678 | 16 | 296.57 | 17.9653 |
| 8 | 5.4466 | 18.9296 | 4319.49 | 0.4041 | 73 | 1815.47 | 18.9052 |
| 9 | 5.3148 | 19.3540 | 2143.38 | 0.4838 | 36 | 1060.13 | 19.3785 |
| 10 | 5.1050 | 20.1728 | 2502.44 | 0.4373 | 42 | 1056.43 | 20.1832 |
| 11 | 4.9607 | 20.7797 | 5335.83 | 0.3688 | 91 | 2177.09 | 20.7764 |
| 12 | 4.7285 | 21.8488 | 636.07 | 38.2172 | 11 | 269.74 | 21.8091 |
| 13 | 4.5431 | 22.7256 | 5310.18 | 0.7702 | 90 | 3045.99 | 22.7108 |
| 14 | 4.4530 | 23.1802 | 3462.25 | 0.4717 | 59 | 1346.82 | 23.1766 |
| 15 | 4.2884 | 24.0652 | 2987.10 | 0.5048 | 51 | 1578.40 | 24.0792 |
| 16 | 4.1009 | 25.1956 | 5888.68 | 0.8595 | 100 | 4621.56 | 25.1978 |
| 17 | 3.9040 | 26.4667 | 456.79 | 0.4214 | 8 | 186.46 | 26.4910 |
| 18 | 3.7434 | 27.6505 | 1774.14 | 0.4150 | 30 | 767.41 | 27.6499 |
| 19 | 3.6319 | 28.5014 | 4389.60 | 0.5018 | 75 | 2312.58 | 28.5162 |
| 20 | 3.4970 | 29.6693 | 786.98 | 0.9137 | 13 | 322.45 | 29.6407 |
| 21 | 3.4424 | 30.1202 | 1186.49 | 0.4386 | 20 | 463.48 | 30.1222 |
| 22 | 3.3386 | 31.0657 | 5624.20 | 0.5631 | 96 | 3840.39 | 31.0817 |
| 23 | 3.1636 | 32.9104 | 830.07 | 1.1216 | 14 | 344.66 | 32.8487 |
| 24 | 3.0981 | 33.5246 | 1343.59 | 0.4286 | 23 | 891.70 | 33.5633 |
| 25 | 2.9942 | 34.7525 | 2763.00 | 0.5357 | 47 | 1698.80 | 34.7644 |
| 26 | 2.8791 | 36.1672 | 1408.74 | 0.6637 | 24 | 995.29 | 36.2011 |
| 27 | 2.8089 | 37.1428 | 428.50 | 0.4051 | 7 | 174.43 | 37.1385 |
| 28 | 2.7226 | 38.3845 | 643.20 | 0.5438 | 11 | 317.55 | 38.3613 |
| 29 | 2.6806 | 39.0598 | 1084.27 | 0.8242 | 18 | 844.28 | 38.9870 |
| 30 | 2.6003 | 40.3103 | 209.49 | 0.4927 | 4 | 92.65 | 40.2409 |
| 31 | 2.5244 | 41.4759 | 627.92 | 0.3926 | 11 | 255.91 | 41.5057 |
| 32 | 2.4873 | 42.1955 | 602.39 | 0.6451 | 10 | 382.81 | 42.1553 |
| 33 | 2.4198 | 43.4221 | 469.36 | 0.5143 | 8 | 239.86 | 43.3888 |
| 34 | 2.3583 | 44.5678 | 552.56 | 0.5226 | 9 | 281.36 | 44.5814 |
| 35 | 2.3067 | 45.6713 | 599.79 | 2.1984 | 10 | 388.97 | 45.6340 |
| 36 | 2.2812 | 46.1477 | 687.26 | 0.6662 | 12 | 408.64 | 46.1729 |
| 37 | 2.2316 | 47.2945 | 267.95 | 0.5005 | 5 | 141.88 | 47.2612 |
| 38 | 2.1791 | 48.4530 | 661.75 | 0.5796 | 11 | 395.13 | 48.4704 |
| 39 | 2.1463 | 49.2375 | 296.69 | 0.4052 | 5 | 113.58 | 49.2604 |
| 40 | 2.0839 | 50.7695 | 461.38 | 0.8775 | 8 | 353.88 | 50.8390 |
| 41 | 2.0376 | 52.2196 | 411.11 | 1.2246 | 7 | 423.01 | 52.0804 |
| 42 | 1.9609 | 54.3435 | 141.90 | 1.1565 | 2 | 151.92 | 54.2815 |
| 43 | 1.9155 | 55.7305 | 137.54 | 0.4928 | 2 | 76.14 | 55.6762 |
| 44 | 1.8923 | 56.4124 | 106.92 | 0.5866 | 2 | 62.03 | 56.4201 |
| 45 | 1.8409 | 58.1406 | 438.55 | 0.9046 | 7 | 350.41 | 58.1449 |

Example 5

Preparation of 5-Methyl-(6S)-tetrahydrofolic acid di N-methylaminoethanol salt 3.00 g (5.30 mmol) of Levomefolinate Calcium was placed under argon in 45 ml water, with a small amount of cysteine and heated to 70° C. The suspension obtained was then treated with 848 μl (10.60 mmol) of N-methylaminoethanol and 668 mg (5.30 mmol) oxalic acid dissolved in 5 ml water. The thin suspension was stirred at 70° C. for additional 5 mins than cooled to 0° C. and stirred for 50 mins. The reaction mixture was filtered, and the clear solution stabilized with a small amount of Cysteine and concentrated at 45° C./<200 mbar. To the remainder seed crystals were added and the product started slowly to crystallize which was completed at 2-8° C. The crystals were dried at 50° C./<1 mbar yielding 3.08 g crude product. The crude product is dissolved in 25 ml methanol, 1.21 ml (3 eq) N-methylaminoethanol and 5 ml 1-propanol. The turbid solution filtered, with 10 ml methanol washed, and the clear filtrate heated to 60° C. Then to the solution was added 65 ml 1-propanol, 150 μl water and 1 eq N-methylaminoethanol. The mixture was treated at 60° C. with seeding crystals to initiate crystallization and then slowly and gradually cooled down from 60° C. down to 0° C. The crystals were sucked off, washed with 1-propanol/methanol 2:1, then with 1-propanol and with ether. The isolated crystals were dried at 50° C./<1 mbar to give 2.60 g of the title compound as off-white crystals. Analytical data:

| δ (1H) in ppm | Multiplicity | Intensity |
|---|---|---|
| 7.55 | d | 2H |
| 6.64 | d | 2H |
| 4.19 | m | 1H |
| 3.73 | t | 4H |
| 3.39 | dd | 1H |
| 3.19 | d | 1H |
| 3.06 | t | 4H |
| 3.01 | m | 1H |
| 2.96 | m | 1H |
| 2.86 | m | 1H |
| 2.63 | s | 6H |
| 2.41 | s | 3H |
| 2.20 | m | 2H |
| 2.04 | m | 1H |
| 1.92 | m | 1H |

Optical rotation: $\alpha^{20D}$ +41.2° (c=1 H$_2$O)

Crystal water in L-MTHF di N-methylaminoethanol (L-MTHF di NMAE): 1.5 (KF and microanalysis)

Melting point: 199° C. (DSC)

X-Ray Diffraction Analysis:

Peaklist of the Diffractogram

| No | d | Ang-COG | I-net | FWHM | I-rel | J-Net | 2-Theta |
|---|---|---|---|---|---|---|---|
| 1 | 15.9239 | 6.4555 | 3447.22 | 0.2915 | 62 | 1310.88 | 6.4404 |
| 2 | 13.2430 | 7.7569 | 342.13 | 0.2693 | 6 | 107.43 | 7.7460 |
| 3 | 10.6647 | 9.6216 | 351.41 | 0.5243 | 6 | 168.18 | 9.6227 |
| 4 | 8.6455 | 11.8830 | 2065.04 | 0.3935 | 37 | 925.99 | 11.8775 |
| 5 | 8.0760 | 12.7075 | 1051.80 | 0.3851 | 19 | 463.22 | 12.7183 |
| 6 | 7.2379 | 14.1946 | 1692.36 | 0.4019 | 30 | 849.92 | 14.1982 |
| 7 | 6.4910 | 15.8352 | 1423.31 | 0.5448 | 26 | 769.40 | 15.8419 |
| 8 | 6.1912 | 16.5964 | 1776.39 | 0.3969 | 32 | 792.92 | 16.6144 |
| 9 | 5.8518 | 17.5782 | 1574.72 | 0.4159 | 28 | 677.72 | 17.5854 |
| 10 | 5.7065 | 18.0117 | 842.39 | 0.2941 | 15 | 320.19 | 18.0368 |
| 11 | 5.5184 | 18.6561 | 331.23 | 0.2270 | 6 | 75.32 | 18.6568 |
| 12 | 5.2649 | 19.5645 | 3100.77 | 0.5100 | 56 | 1789.83 | 19.5639 |
| 13 | 4.9150 | 20.8504 | 2849.68 | 0.8527 | 51 | 2518.15 | 20.9719 |
| 14 | 4.4919 | 22.9765 | 1560.48 | 0.5605 | 28 | 740.63 | 22.9732 |
| 15 | 4.3400 | 23.7913 | 5552.11 | 0.5205 | 100 | 3197.94 | 23.7886 |
| 16 | 4.1843 | 24.6733 | 1784.30 | 0.7474 | 32 | 985.69 | 24.6875 |
| 17 | 4.0907 | 25.2464 | 2221.96 | 0.7649 | 40 | 1019.95 | 25.2619 |
| 18 | 4.0153 | 25.7631 | 1954.24 | 54.7000 | 35 | 921.46 | 25.7440 |
| 19 | 3.9450 | 26.2167 | 2046.11 | 7.5545 | 37 | 1004.46 | 26.2108 |
| 20 | 3.8277 | 27.0229 | 2110.05 | 0.3186 | 38 | 1302.24 | 27.0293 |
| 21 | 3.6080 | 28.7332 | 2331.17 | 1.1356 | 42 | 1515.86 | 28.7091 |
| 22 | 3.5644 | 29.0745 | 2481.56 | 0.6321 | 45 | 907.72 | 29.0680 |
| 23 | 3.5241 | 29.5119 | 1950.57 | 0.6549 | 35 | 879.22 | 29.4083 |
| 24 | 3.3363 | 31.1061 | 1592.05 | 0.4227 | 29 | 764.29 | 31.1042 |
| 25 | 3.2265 | 32.1838 | 445.10 | 0.4686 | 8 | 191.02 | 32.1902 |
| 26 | 3.0955 | 33.5791 | 1288.22 | 0.6295 | 23 | 842.12 | 33.5921 |
| 27 | 3.0000 | 34.6824 | 424.90 | 0.3412 | 8 | 138.72 | 34.6950 |
| 28 | 2.8727 | 36.3015 | 582.88 | 0.9961 | 10 | 502.22 | 36.2851 |
| 29 | 2.8013 | 37.1978 | 392.89 | 0.4582 | 7 | 162.25 | 37.2432 |
| 30 | 2.6370 | 39.6821 | 342.70 | 0.9931 | 6 | 284.71 | 39.6573 |
| 31 | 2.5222 | 41.6802 | 376.12 | 0.7416 | 7 | 319.37 | 41.5443 |
| 32 | 2.4135 | 43.6281 | 295.28 | 1.0135 | 5 | 239.40 | 43.5694 |
| 33 | 2.3135 | 45.3960 | 385.86 | 0.9283 | 7 | 311.87 | 45.4926 |
| 34 | 2.0336 | 52.2798 | 182.37 | 0.8020 | 3 | 232.56 | 52.1894 |
| 35 | 1.8353 | 58.3600 | 257.19 | 0.6312 | 5 | 125.39 | 58.3372 |

Solubilities:

| L-MTHF di NMAE | Methanol | Ethanol | 1-Propanol | DMSO | Glycerol |
|---|---|---|---|---|---|
| as % w/w | 3.6 | 0.2 | 0.1 | 3.5 | 16.7 |

Example 6

Preparation of 5-Methyl-(6S)-tetrahydrofolic acid di 2-Amino-2-methyl propanol salt 3.00 g (5.30 mmol) of Levomefolinate Calcium was placed under argon in 45 ml Water with small amounts of cysteine and heated to 70° C. This suspension was then treated with 1012 μl (10.60 mmol) of 2-amino-2-methylpropanol and 668 mg (5.30 mmol) oxalic acid dissolved in 5 ml water. At 70° C. the thin suspension was stirred for 5 mins than cooled to 0° C. The thin suspension was filtered, and the solution stabilized with cystein and concentrated at 45° C./<200 mbar. The remainder is treated with seed crystals and crystallization completed over night at 2-8° C. The crystals were dried at 50° C./1 mbar. The crude product was dissolved in 6.5 ml water and heated to 70° C . The solution was diluted with 70 ml 1-propanol (10.4% water in 1-propanol), treated with seed crystals and slowly and gradually cooled to 20-23° C. The crystals were isolated and washed with 1-propanol/water 20:1 (v/v), 1-propanol and ether and dried at 50° C./<1 mbar to give 2.79 g of the title compound as off-white crystals. Analytical data:

| δ (1H) in ppm | Multiplicity | Intensity |
|---|---|---|
| 7.61 | d | 2H |
| 6.70 | d | 2H |
| 4.25 | m | 1H |
| 3.49 | s | 4H |
| 3.45 | dd | 1H |
| 3.25 | d | 1H |
| 3.08 | m | 1H |
| 3.03 | m | 1H |
| 2.93 | m | 1H |
| 2.48 | s | 3H |
| 2.24 | m | 2H |
| 2.09 | m | 1H |
| 1.96 | m | 1H |
| 1.25 | s | 1H |

Optical rotation: $\alpha^{20D}$ +34.6° (c=1 H$_2$O)
Crystal water in L-MTHF di 2-amino-2-methylpropanol: 1.5 (KF and microanalysis)
X-Ray Diffraction Analysis:
Peaklist of the Diffractogram

| No | d | Ang-COG | I-net | FWHM | I-rel | J-Net | 2-Theta |
|---|---|---|---|---|---|---|---|
| 1 | 16.9589 | 6.0659 | 1948.86 | 0.3358 | 40 | 861.63 | 6.0470 |
| 2 | 10.7625 | 9.5378 | 1271.39 | 0.4369 | 26 | 730.38 | 9.5351 |
| 3 | 8.5244 | 12.0441 | 565.44 | 0.4056 | 12 | 235.94 | 12.0468 |
| 4 | 7.6831 | 13.3727 | 593.37 | 0.3334 | 12 | 226.12 | 13.3716 |
| 5 | 6.9490 | 14.8004 | 1067.54 | 0.4564 | 22 | 546.58 | 14.7916 |
| 6 | 6.3851 | 16.0496 | 1711.61 | 0.7491 | 35 | 842.29 | 16.1064 |
| 7 | 6.2391 | 16.4806 | 1858.51 | 0.4576 | 38 | 838.10 | 16.4859 |
| 8 | 5.7750 | 17.8155 | 2430.06 | 0.7075 | 50 | 1790.36 | 17.8211 |
| 9 | 5.4350 | 18.9458 | 1719.22 | 0.4026 | 35 | 745.79 | 18.9460 |
| 10 | 5.1688 | 19.9140 | 1561.56 | 0.4133 | 32 | 699.72 | 19.9315 |
| 11 | 4.9968 | 20.6591 | 1530.23 | 1.9946 | 31 | 776.03 | 20.6246 |
| 12 | 4.8365 | 21.3238 | 3675.03 | 1.4192 | 75 | 2664.97 | 21.3161 |
| 13 | 4.6770 | 22.0378 | 3176.73 | 0.7791 | 65 | 1761.55 | 22.0522 |
| 14 | 4.5111 | 22.8596 | 4898.09 | 0.7549 | 100 | 3428.98 | 22.8737 |
| 15 | 4.3934 | 23.4643 | 2400.39 | 0.4554 | 49 | 1223.98 | 23.4953 |
| 16 | 4.0694 | 25.4175 | 1303.78 | 0.4489 | 27 | 651.63 | 25.3961 |
| 17 | 3.8398 | 26.8492 | 1292.38 | 0.9049 | 26 | 1144.63 | 26.9426 |
| 18 | 3.6304 | 28.5953 | 514.86 | 0.9570 | 11 | 345.40 | 28.5279 |
| 19 | 3.4132 | 30.1026 | 964.08 | 1.3324 | 20 | 1230.83 | 30.3861 |
| 20 | 3.2554 | 31.9288 | 1299.61 | 0.7547 | 27 | 1160.53 | 31.8976 |
| 21 | 3.1203 | 33.3269 | 752.36 | 1.0566 | 15 | 744.16 | 33.3176 |
| 22 | 2.9704 | 35.0505 | 339.01 | 0.6687 | 7 | 226.11 | 35.0518 |
| 23 | 2.8466 | 36.5760 | 999.03 | 1.1577 | 20 | 1112.09 | 36.6287 |
| 24 | 2.6992 | 38.6950 | 656.44 | 0.6515 | 13 | 430.95 | 38.7063 |
| 25 | 2.5723 | 40.7894 | 540.59 | 0.8748 | 11 | 421.04 | 40.6993 |
| 26 | 2.4455 | 42.9257 | 322.63 | 0.8876 | 7 | 229.25 | 42.9106 |
| 27 | 2.3190 | 45.3614 | 400.77 | 1.0942 | 8 | 474.93 | 45.3788 |
| 28 | 2.1088 | 50.1810 | 404.87 | 1.2316 | 8 | 398.23 | 50.1977 |

Solubilities:

| L-MTHF di AMP | Methanol | Ethanol | 1-Propanol | DMSO | Glycerol |
|---|---|---|---|---|---|
| as % w/w | 11.2 | 0.1 | 0.1 | 23.1 | 16.7 |

Example 7

Preparation of Cholin Hydroxide Solution Used in Example 2

10.39 g (74.42 mmol) of Choline chloride was placed under argon in a solution of 110 ml 1-Propanol and 3.02 g (74.42 mmol) sodium hydroxide at 20-25° C. The mixture was heated to 70-72° C. for ca 70 mins and heated to 70° C. This suspension was then cooled to 0-5° C. for 45 mins. The white suspension was filtered through a silica bed and the filtrate filled up in a volumetric flask up to 200 ml with 1-propanol. The concentration of choline hydroxide was 0.36 mol/l (as measured by titration)

This solution was used as storage form of choline used for preparation of highly pure choline salts of folates.

The invention claimed is:

1. A crystalline folate salt comprising a tetrahydrofolic acid anion and an organic cation where the anion is 5-methyl-(6S)-tetrahydrofolic acid, and the cation is an organic compound wherein the organic compound is an alkanolamine selected from the group consisting of 2-dimethylaminoethanol, N-methylaminoethanol, and 2-amino-2methylpropanol.

2. The crystalline folate salt according to claim 1, wherein the folate salts have a solubility of higher than 2 weight-% (w/w) based on a total weight of a solution at 20° C. in organic solvents.

3. The crystalline folate salt according to claim 1, wherein the organic compound is mono-2-dimethylaminoethanol.

4. The crystalline folate salt according to claim 1, wherein the organic compound is di 2-dimethylaminoethanol.

5. The crystalline folate salt according to claim 1, wherein the organic compound is di-N-methylaminoethanol.

6. The crystalline folate salt according to claim 1, wherein the organic compound is di-2-amino-2-methylpropanol.

7. The crystalline folate salt according to claim 1, wherein the tetrahydrofolic acid anion is 5-methyl-(6S)-tetrahydrofolic acid and the organic cation is 2-methylaminoethanol.

8. A pharmaceutical composition, comprising at least one folate salt according to claim 1, as a main active compound and at least a pharmaceutically acceptable excipient.

9. A method of preparing the crystalline folate salt according to claim 1, comprising crystallizing a folate salt comprising a tetrahydrofolic acid anion and an organic cation from an organic solvent comprising water in a range of 0.2 weight-% to 12 weight-% based on a weight of the organic solvent comprising the water.

10. A method of treating deficiencies or disorders that are positively affected by the administration of a tetrahydrofolic acid salt, comprising administering the crystalline folate salt according to claim 1 to a patient in need thereof.

11. A method of preventing deficiencies or disorders that are positively affected by the administration of a tetrahydrofolic acid salt, comprising administering the crystalline folate salt according to claim 1 to a patient in need thereof.

* * * * *